(12) United States Patent
Fraser et al.

(10) Patent No.: US 9,198,680 B2
(45) Date of Patent: Dec. 1, 2015

(54) COMBINATION IMAGING AND THERAPY TRANSDUCER WITH THERAPY TRANSDUCER AMPLIFIER

(75) Inventors: John Fraser, Woodinville, WA (US); Jeffry E. Powers, Bainbridge Island, WA (US); Michalakis Averkiou, Nicosia (CY)

(73) Assignee: Koninklijke Philips N.V., Eindhoven (NL)

( * ) Notice: Subject to any disclaimer, the term of this patent is extended or adjusted under 35 U.S.C. 154(b) by 1733 days.

(21) Appl. No.: 12/064,309

(22) PCT Filed: Aug. 25, 2006

(86) PCT No.: PCT/IB2006/052966
§ 371 (c)(1),
(2), (4) Date: Feb. 20, 2008

(87) PCT Pub. No.: WO2007/026300
PCT Pub. Date: Mar. 8, 2007

(65) Prior Publication Data
US 2008/0228075 A1 Sep. 18, 2008

Related U.S. Application Data

(60) Provisional application No. 60/712,316, filed on Aug. 30, 2005.

(51) Int. Cl.
*A61B 8/00* (2006.01)
*A61B 8/12* (2006.01)
(Continued)

(52) U.S. Cl.
CPC ......... *A61B 17/22004* (2013.01); *A61B 8/0833* (2013.01); *A61B 8/14* (2013.01);
(Continued)

(58) Field of Classification Search
CPC ........ A61B 8/0833; A61B 8/14; A61B 8/481; A61B 4/4405; A61B 17/2256; A61B 17/22004; A61B 2017/22028; A61B 2019/5276; G01S 15/8918; G01S 15/8977
See application file for complete search history.

(56) References Cited

U.S. PATENT DOCUMENTS 4,484,569 A   11/1984   Driller et al.
4,932,414 A    6/1990   Coleman et al.
(Continued)

FOREIGN PATENT DOCUMENTS

EP   0659387 A2   6/1995
JP   1099541 A    4/1989
(Continued)

*Primary Examiner* — Long V Le
*Assistant Examiner* — Colin T Sakamoto (57) ABSTRACT

A combined ultrasound imaging and therapy transducer (10) includes a linear array of imaging transducer elements (14). First and second linear arrays of therapy transducer elements (18, 20) extend longitudinally along respective first and second sides of the imaging transducer elements and are canted inwardly toward each other. The imaging and therapy transducer is used with an ultrasound imaging system to locate clots in a region of interest. After the region of interest has been perfused with a microbubble contrast agent, the therapy transducer elements are driven by an amplifier located in the transducer to dissolve the clot. The use of the imaging transducer elements and the therapy transducer elements can be interleaved so that the therapy can be conditioned on an ultrasound image showing substantial destruction of the contrast agent microbubbles, re-perfusion of microbubbles in the region of interest, or the continued presence of the clot.

13 Claims, 6 Drawing Sheets (51) Int. Cl.
  *A61B 17/22* (2006.01)
  *A61B 8/08* (2006.01)
  *A61B 8/14* (2006.01)
  *A61B 17/225* (2006.01)
  *G01S 15/89* (2006.01)
  *A61B 19/00* (2006.01)

(52) U.S. Cl.
  CPC ............ *A61B 8/481* (2013.01); *A61B 17/2256* (2013.01); *G01S 15/8918* (2013.01); *G01S 15/8977* (2013.01); *A61B 8/4405* (2013.01); *A61B 2017/22028* (2013.01); *A61B 2019/5276* (2013.01)

(56) References Cited

U.S. PATENT DOCUMENTS

| | | | |
|---|---|---|---|
| 5,005,579 A | | 4/1991 | Wurster et al. |
| 5,142,649 A | * | 8/1992 | O'Donnell ............... 367/7 |
| 5,471,988 A | * | 12/1995 | Fujio et al. ............ 600/439 |
| 6,468,216 B1 | * | 12/1995 | Fujio et al. ............ 600/439 |
| 5,558,092 A | | 9/1996 | Unger et al. |
| 5,769,790 A | * | 6/1998 | Watkins et al. ......... 600/439 |
| 5,873,828 A | * | 2/1999 | Fujio et al. ............ 600/439 |
| 6,050,943 A | * | 4/2000 | Slayton et al. ......... 600/439 |
| 6,296,619 B1 | * | 10/2001 | Brisken et al. ............ 604/22 |
| 6,428,477 B1 | * | 8/2002 | Mason .................... 600/437 |
| 6,471,649 B1 | * | 10/2002 | Saccardo et al. .......... 600/437 |
| 6,537,224 B2 | | 3/2003 | Mauchamp et al. |
| 6,719,694 B2 | * | 4/2004 | Weng et al. ............. 600/439 |
| 7,470,241 B2 | * | 12/2008 | Weng et al. ............. 601/3 |
| 7,862,511 B2 | * | 1/2011 | Rafter ................... 600/458 |
| 2001/0031922 A1 | * | 10/2001 | Weng et al. ............. 600/439 |
| 2003/0097069 A1 | * | 5/2003 | Avinash et al. ........... 600/447 |
| 2003/0107888 A1 | | 6/2003 | Devlin |
| 2003/0204141 A1 | * | 10/2003 | Nock et al. .............. 600/439 |
| 2004/0122323 A1 | * | 6/2004 | Vortman et al. ........... 600/459 |
| 2004/0254620 A1 | | 12/2004 | Lacoste et al. |
| 2005/0038340 A1 | * | 2/2005 | Vaezy et al. ............ 600/439 |
| 2005/0119574 A1 | * | 6/2005 | Maerfeld et al. .......... 600/459 |
| 2005/0148873 A1 | * | 7/2005 | Petersen et al. .......... 600/447 |
| 2006/0058707 A1 | * | 3/2006 | Barthe et al. ............ 601/2 |
| 2008/0183077 A1 | * | 7/2008 | Moreau-Gobard et al. .. 600/439 |
| 2008/0287835 A1 | * | 11/2008 | Zhao et al. .............. 601/2 |

FOREIGN PATENT DOCUMENTS

| | | |
|---|---|---|
| JP | 0592001 A | 4/1993 |
| JP | 10216145 A | 8/1998 |
| JP | 2000189521 A | 7/2000 |
| JP | 2001037772 A | 2/2001 |
| JP | 2001333900 A | 12/2001 |
| JP | 2002263105 A | 9/2002 |
| WO | 00/61007 A | 10/2000 |
| WO | 2004100617 A | 11/2004 |

* cited by examiner

COMBINATION IMAGING AND THERAPY TRANSDUCER WITH THERAPY TRANSDUCER AMPLIFIER

This invention relates to the fields of ultrasound imaging and therapy, and more particularly, to a method and apparatus for providing ultrasound images and ultrasound therapy on the same region of a patient's anatomy at essentially the same time.

Diagnostic ultrasound involves the imaging of a region of a patient's anatomy using an ultrasound transducer to generate and receive ultrasound energy. Typically, an ultrasound transducer is placed on the patient's skin, and ultrasound energy is transmitted into a region of interest beneath the transducer. The transducer then receives reflected ultrasound from the region of interest and converts the received ultrasound into electrical signals. The electrical signals are then processed to generate an image, which may be presented on a display.

Contrast agents can be used to improve the quality of diagnostic ultrasound images. Contrast agents include, for example, suspensions of solid particles, emulsified liquid droplets, and gas-filled bubbles, known as "microbubbles." All of these contrast agents intensify the reflections of ultrasound because they create large acoustic discontinuities between the contrast agents and the surrounding blood or tissue. Each of the different types of contrast agents has its advantages and disadvantages. For example, microbubble contrast agents have the disadvantage of being somewhat fragile and therefore can be easily fractured by ultrasound energy.

Ultrasound is presently under development for various therapeutic applications. One therapeutic use of ultrasound is known as hyperthermia. Hyperthermia involves insonating a targeted tissue mass, such as a tumor, with focused ultrasound for the purpose of heating the targeted mass. Application of heat to the tissue mass results in a retardation of growth of, or a shrinking of, the mass.

Another therapeutic use of ultrasound involves administering a quantity of vesicles to a patient and monitoring the vesicles, for example using diagnostic ultrasound, until the presence of the vesicles is detected in a region of interest. Higher intensity therapeutic ultrasound is then applied to the region to rupture the vesicles for therapeutic purposes. For example, the vesicles may be combined with a bioactive agent that is released upon rupture of the vesicles. This technique is therefore capable of achieving targeted delivery of the bioactive agent in the region of interest.

High-intensity ultrasound is also being used experimentally with the ultrasonic energy focused to a subcutaneous depth where internal bleeding is occurring. This technique heats and thus coagulates the tissues at the depth to which the ultrasound is focused to stop the internal bleeding. High-intensity focused ultrasound, referred to as "HIFU", is being used in some countries to kill tumor cells by heating.

Ultrasound is also being used experimentally to dissolve clots in blood vessels, such as the deep blood vessels of the leg, for the purpose of treating deep venous thrombosis ("DVT"). Studies have shown that a blood vessel clot can be dissolved using ultrasound before it has separated from the vessel and traveled to the lungs. Ultrasound can also be used in this same manner to treat peripheral artery disease. Studies have also shown that ultrasound can be used more effectively for these purposes if a microbubble contrast agent has been introduced into the vein containing the clot or the diseased artery. The ultrasound breaks up the microbubbles, and the destruction of the microbubbles apparently provides agitation to a greater extent than is possible using ultrasound alone.

Therapeutic ultrasound is typically carried out at different frequencies than diagnostic ultrasound. Specifically, it is desirable to perform therapeutic ultrasound at lower frequencies in order to achieve low attenuation. In contrast, higher frequencies are employed in diagnostic ultrasound to obtain better image resolution. As a result, it is generally not practical to use the same ultrasound transducer for both imaging and therapy. Therefore, an imaging transducer is normally used to locate a site where therapeutic ultrasound is needed. Once the treatment site is located, a therapeutic transducer is used to administer the therapeutic ultrasound.

These approaches for administering therapeutic ultrasound have many limitations and shortcomings. In many cases, a practitioner administering the therapy is not able to position the therapeutic transducer at the exact location of the treatment site identified by using the imaging transducer. Also, by not being able to image the treatment site while the therapy is being applied, it can be difficult to determine when the clot has been dissolved and the therapy can be discontinued. Similarly, if the clot has not dissolved in response to a sequence of pulses of therapeutic ultrasound, it can be difficult and time consuming to re-image the treatment site to determine if pulses of therapeutic ultrasound should be repeated.

There has been some effort in the prior art to provide systems that permit diagnostic ultrasound to be carried out essentially simultaneously with therapeutic ultrasound, particularly therapeutic applications involving hyperthermia. For example, U.S. Pat. No. 5,558,092 to Unger et al. describes a combined imaging and therapy transducer for use in rupturing vesicles for the targeted release of a bioactive agent. Several transducer embodiments are shown in which a set of therapy transducer elements are surrounded by imaging transducer elements. Similarly, U.S. Pat. No. 5,391,140 to Schaetzle, et al., describes an apparatus having a diagnostic ultrasound capability that operates simultaneously with the application of therapeutic acoustic waves for localized hyperthermia. The system employs a transducer assembly that includes a set of imaging transducer elements surrounded by therapeutic transducer elements. Other ultrasound systems that include a transducer combining imaging and therapeutic capabilities are described in U.S. Pat. No. 4,484,569 to Driller et al., U.S. Pat. No. 4,932,414 Coleman et al., and U.S. Pat. No. 5,005,579 Wurster et al.

The prior art transducers described in these patents all exhibit some structure that limits their utility in accurately delivering therapeutic ultrasound having a uniform intensity to a treatment site and allowing the therapy to be monitored during treatment. Furthermore, to the extent that any of these transducers are capable of imaging and providing therapy at substantially the same time, the prior art does not recognize techniques for taking advantage of this capability to quickly and easily determine when to continue and to discontinue the ultrasound therapy.

A combined ultrasound imaging and therapy transducer includes a linear array of imaging transducer elements extending longitudinally in an azimuthal direction. First and second linear arrays of therapy transducer elements extend longitudinally in an azimuthal direction along respective first and second sides of the linear array of imaging transducer elements. The therapy transducer elements in the linear array are canted inwardly toward the imaging transducer elements to direct therapeutic ultrasound to a localized depth. The imaging and therapy transducer may be used with an ultrasound system to dissolve clots in veins that have been perfused with a microbubble contrast agent. The ultrasound system includes an ultrasound signal path coupled to the imaging transducer elements. The ultrasound signal path transmits electrical signals to the imaging transducer elements to cause the imaging transducer elements to transmit ultrasound into a region of interest beneath the imaging transducer elements. The ultrasound signal path also receives electrical signals indicative of ultrasound reflections from the region of interest and processes the received electrical signals to provide an ultrasound image on a display. The ultrasound system also includes a high-intensity transmitter coupled to the therapy transducer elements to apply high-intensity electrical signals to the therapy transducer elements.

Figure 1:
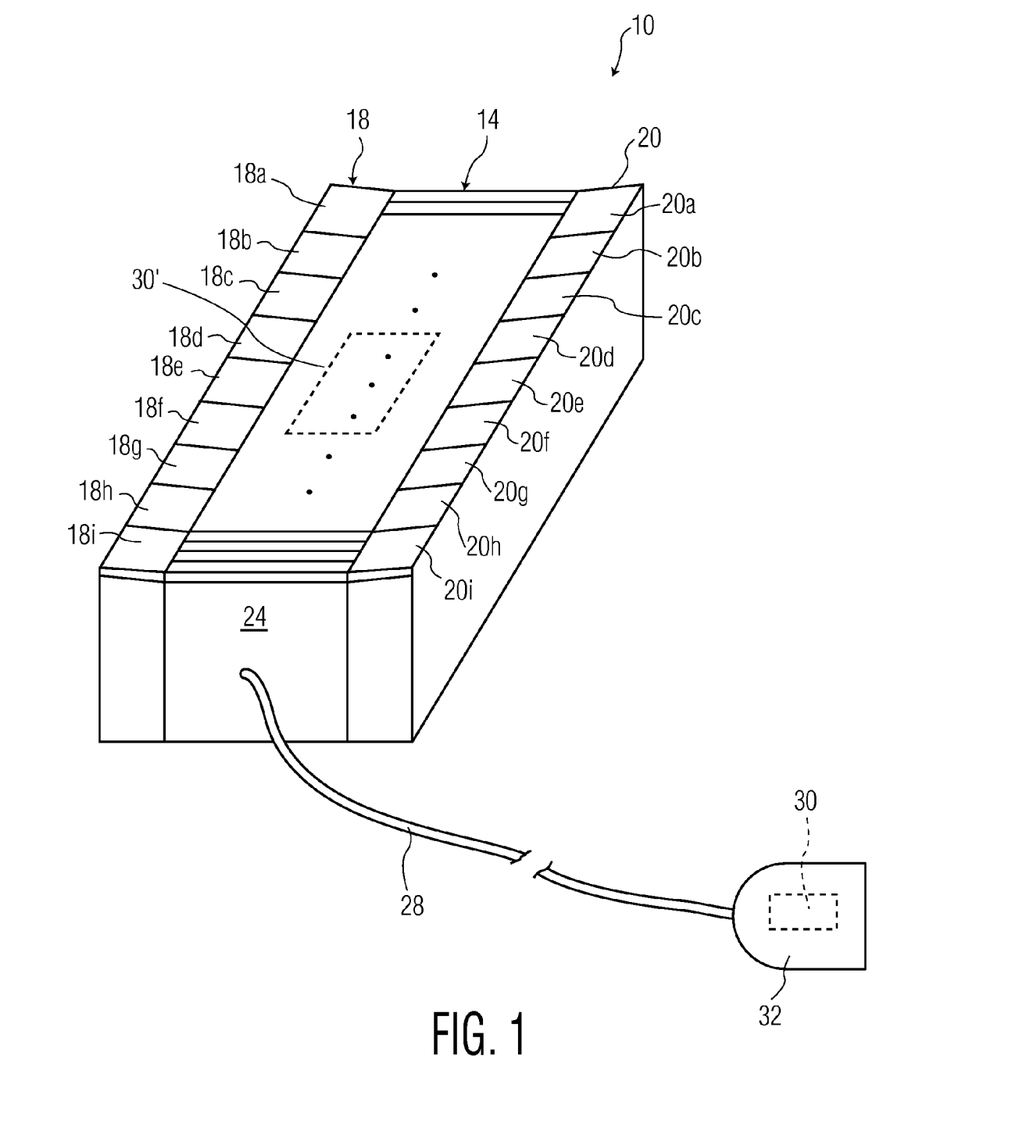
FIG. 1 is an isometric view showing a combined imaging and therapy ultrasound transducer according to one example of the invention.

A combined ultrasound imaging and therapy transducer 10 according to one example of the invention is shown in FIG. 1. The transducer 10 includes a linear array of imaging elements 14 extending along the center of the transducer 10. Therapy transducer elements 18, 20 are positioned on opposite sides of the imaging elements 14. The transducer elements 18, 20 are segmented in the azimuthal direction to form a pair of linear arrays of transducer elements 18a-i, 20a-i. The therapy elements 18, 20 are canted inwardly at a slight angle toward the imaging elements 14. Canting the therapy elements 18, 20 inwardly helps focus the therapeutic ultrasound beneath the imaging elements 14 to a localized depth. As a result, the therapeutic ultrasound can be accurately positioned at a treatment site identified during imaging. In a given implementation the therapy transducer elements may not extend the full length of the imaging array but only along a portion thereof, such as being located on either side of the central portion of the imaging array.

The imaging elements 14 and the therapy elements 18, 20 are mounted on a base 24 from which a cable 28 extends. A high-intensity radio frequency ("RF") amplifier 30 is preferably mounted in the connector 32 at the end of the cable for supplying high-intensity electrical signals to the therapy elements 18, 20. The connector is used to connect the ultrasound probe to an ultrasound system which controls operation of the probe and displays the images produced by echo signals from the probe. The RF amplifier 30' can alternatively be located in the transducer assembly as shown in phantom in FIG. 1, however heat developed by the amplifier can be more easily and safely disbursed from the connector 32.

In operation, the imaging elements 14 are scanned starting at one end by stepping from a one set of imaging elements 14 to the next until the opposite end is reached. During stepping, the adjacent sets of imaging elements 14 that are active preferably overlap each other to a substantial extent. For example, in the transducer 10 having 192 imaging elements 14, each set may include 50 imaging elements 14. The number of scan lines created during transmission of ultrasound from the imaging elements 14 may be the same as or different from the number of scan lines created while the imaging elements 14 receive ultrasound. In one example, the steps are chosen so that 128 transmit scan lines and 256 receive scan lines are created.

Figure 2:
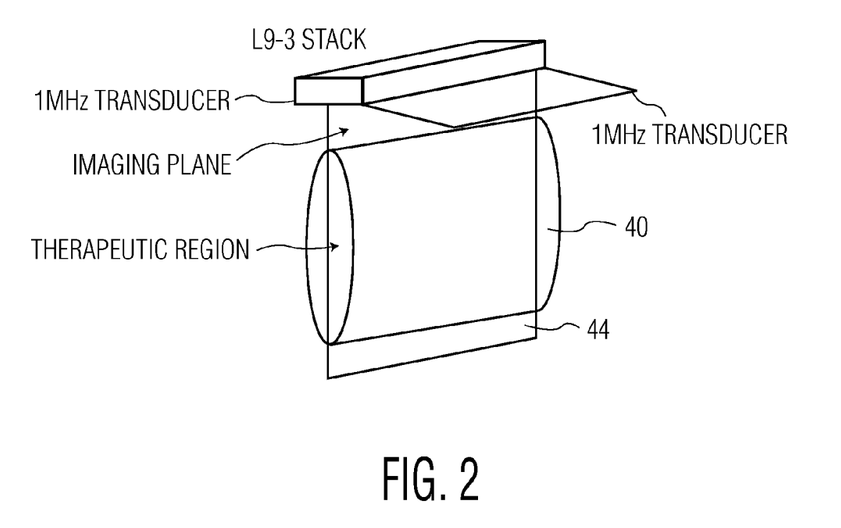
FIG. 2 is a schematic diagram showing the ultrasound imaging and the therapy patterns of the transducer of FIG. 1.

An ultrasound system (not shown in FIG. 1) to which the imaging elements 14 are coupled preferably delays the signals applied to and received from the imaging elements 14 to focus the transmitted and received ultrasound to controlled depths. With reference also to FIG. 2, the ultrasound echoes received by the imaging elements 14 allows a two-dimensional image to be created in which the echoes from anatomic structures in a therapeutic region 40 (FIG. 2) beneath the imaging elements 14 are projected onto an imaging plane 44. The echoes projected onto the imaging plane 44 can then be viewed on a display in the ultrasound system (not shown in FIG. 2) to accurately locate the transducer 10 above a treatment site in need of ultrasound therapy. The ultrasound system may also delay the signals applied to and received from the imaging elements 14 to focus the transmitted and received ultrasound to a specific depth in the imaging plane 44 and/or to steer the beams of the transmitted and received ultrasound.

During therapy, the RF amplifier 30 (FIG. 1) supplies the high-intensity electrical signals to one or a few of the therapy elements 18, 20 at a time. Therapy then proceeds in stepwise fashion. For example, the electrical signals may first be applied to the elements 18a,b and 20a,b, followed by 18b,c and 20b,c, followed by 18c,d and 20c,d, and so forth until the electrical signals are applied to the elements 18h,i and 20h,i. If the high-intensity electrical signals were simultaneously supplied to all of the therapy elements 18, 20, the ultrasound from the elements 18 might interfere with each other as would the ultrasound from the elements 20, thereby creating near field distortion. This near field distortion could expose the therapeutic region to uneven ultrasound intensities, particularly close to the transducer 10. As mentioned above, the inward canting of the therapy elements 18, 20 causes the therapeutic ultrasound to be centered at a specific depth in the imaging plane 44, although the therapeutic ultrasound extends throughout the therapeutic region 40. In one example of the transducer 10, the maximum intensity in the middle of the imaging plane 44 is at a depth of between 2 cm. and 6 cm. As an alternative to physically tilting the therapy elements toward the therapy focal point lenses can be employed to steer the therapy waves to the desired focal range.

The segmentation of the therapy elements 18a-i, 20a-i in the azimuthal direction allows the ultrasound transmitted by the elements 18a-i, 20a-i to be delayed relative to each other for the purpose of either steering the therapeutic ultrasound in the azimuth direction or further focusing the therapeutic ultrasound to a desired depth in the imaging plane 44.

In the transducer 10 of FIG. 1, the ultrasound is transmitted from the imaging elements 14 at 6 MHz, and the ultrasound is transmitted from the therapy elements 18, 20 at 1 MHz. However, other frequencies can alternatively be used.

Figure 3:
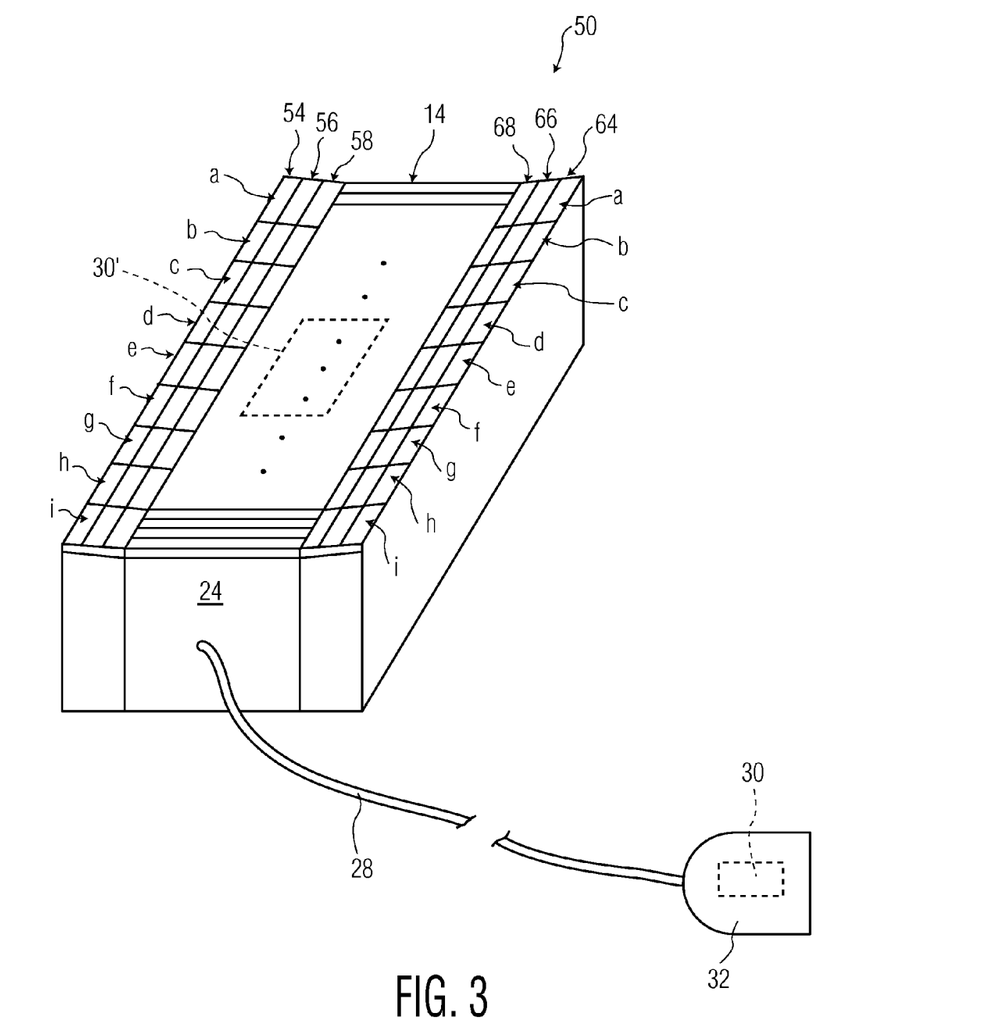
FIG. 3 is an isometric view showing a combined imaging and therapy ultrasound transducer according to another example of the invention.

Another example of a combined ultrasound imaging and therapy transducer 50 is shown in FIG. 3. The transducer 50 is substantially identical to the transducer 10 shown in FIG. 1. Therefore, the identical structural features have been provided with the same reference numerals, and a description of their structure and operation will not be repeated. The transducer 50 differs from the transducer 10 by including therapy transducer elements that are segmented in the azimuthal direction as well as in the elevational direction to form separate sub-elements 54, 56, 58 on one side of the imaging elements 14 and separate sub-elements 64, 66, 68 on the other side of the imaging elements 14.

In operation, the ultrasound is transmitted by the elements 54, 56, 58 and 64, 66, 68 in stepwise fashion in the same manner as described above for the transducer 10. Specifically, the electrical signals may first be applied to the elements 54-58*a,b* and 64-68*a,b*, followed by 54-58*b,c* and 64-68*b,c*, and so forth until the electrical signals are applied to the elements 54-58*h,i* and 64-68*h,i*. However, the electrical signals are transmitted from the therapy transducer elements 54, 56, 58 and 64, 66, 68 with respective delays. More specifically, the signals are transmitted by the elements 54, 64 with a first delay relative to the delay of the signals transmitted by the elements 56, 66, respectively. Similarly, the signals are transmitted by the elements 56, 66 with a first delay relative to the delay of the signals transmitted by the elements 58, 68, respectively. These delays allow the therapy elements 54, 56, 58 and 64, 66, 68 to focus to a specific depth in the imaging plane 44 (FIG. 2). The segmentation of the therapy elements 18*a-i*, 20*a-i* in the azimuthal direction also allows the ultrasound transmitted by the elements 18*a-i*, 20*a-i* to be delayed relative to each other for the purpose of either steering the therapeutic ultrasound in the azimuthal direction or focusing in the depth direction. The therapeutic ultrasound can therefore be delivered to the exact treatment site that was identified during imaging.

Figure 4:
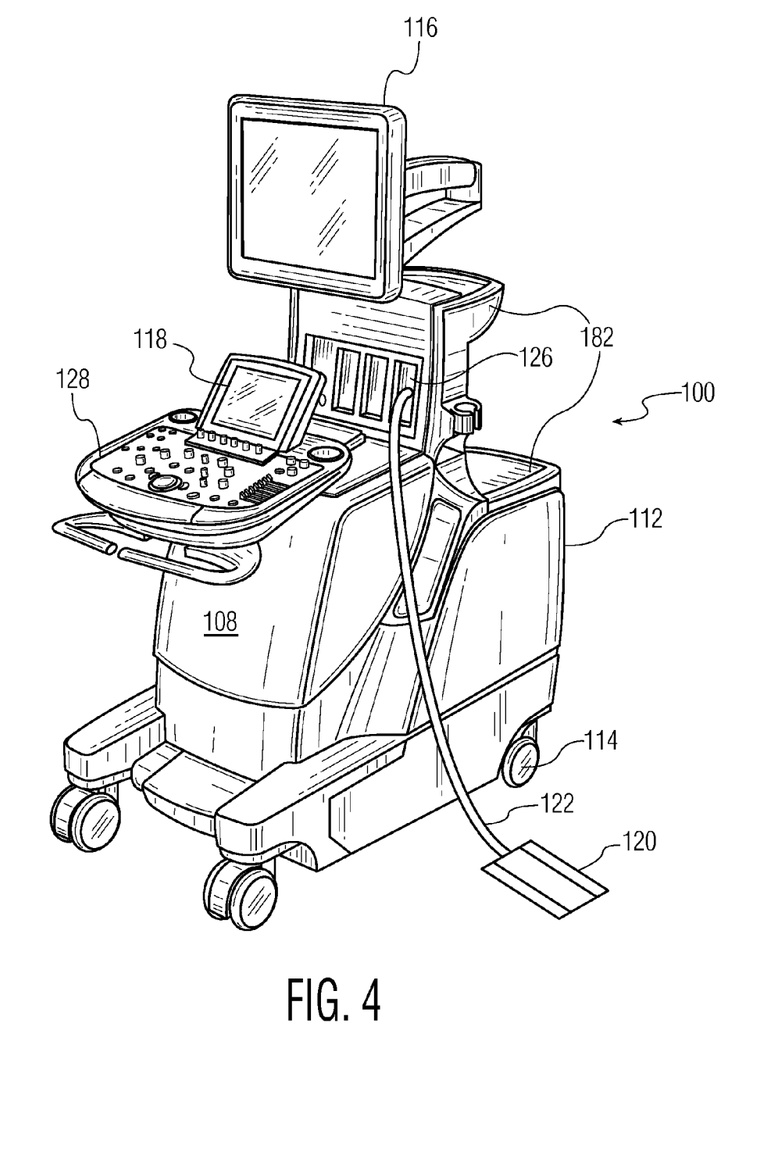
FIG. 4 is an isometric view of an ultrasound system connected to a transducer in accordance with one example of the invention, such as the transducers shown in FIGS. 1 and 3.

An ultrasound system 100 that can be used with the transducer probes 10, 50 or a transducer probe according to some other example of the invention is shown in FIG. 4. The system 100 includes a chassis 108 containing most of the electronic circuitry for the system 100. The chassis 108 is mounted on a cart 112 supported by wheels 114, and a display 116 is mounted on the chassis 108. At the rear of the cart are shelves 182 for accessory equipment. A transducer probe 120, such as one including the transducer 10 or 50 or a transducer according to some other example of the invention, is connected through a cable 122 to a connector 126 on the chassis 108.

The chassis 108 also includes a keyboard and controls, generally indicated by reference numeral 128, for allowing a sonographer to operate the ultrasound system 100 and enter information about the patient or the type of examination and therapy being conducted. At the back of the control panel 128 is a touchscreen display 118 on which programmable softkeys are displayed for supplementing the keyboard and controls 128 in controlling the operation of the system 100.

In operation, the transducer probe 120 is placed against the skin of a patient (not shown) and held stationary to acquire an image of blood or tissues in a region of interest beneath the skin. Once a treatment site has been identified in the acquired image, signals are applied to the therapy elements to direct high-intensity therapeutic ultrasound to the identified treatment site. Specific techniques for performing imaging and providing therapy will be discussed in greater detail below.

Figure 5:
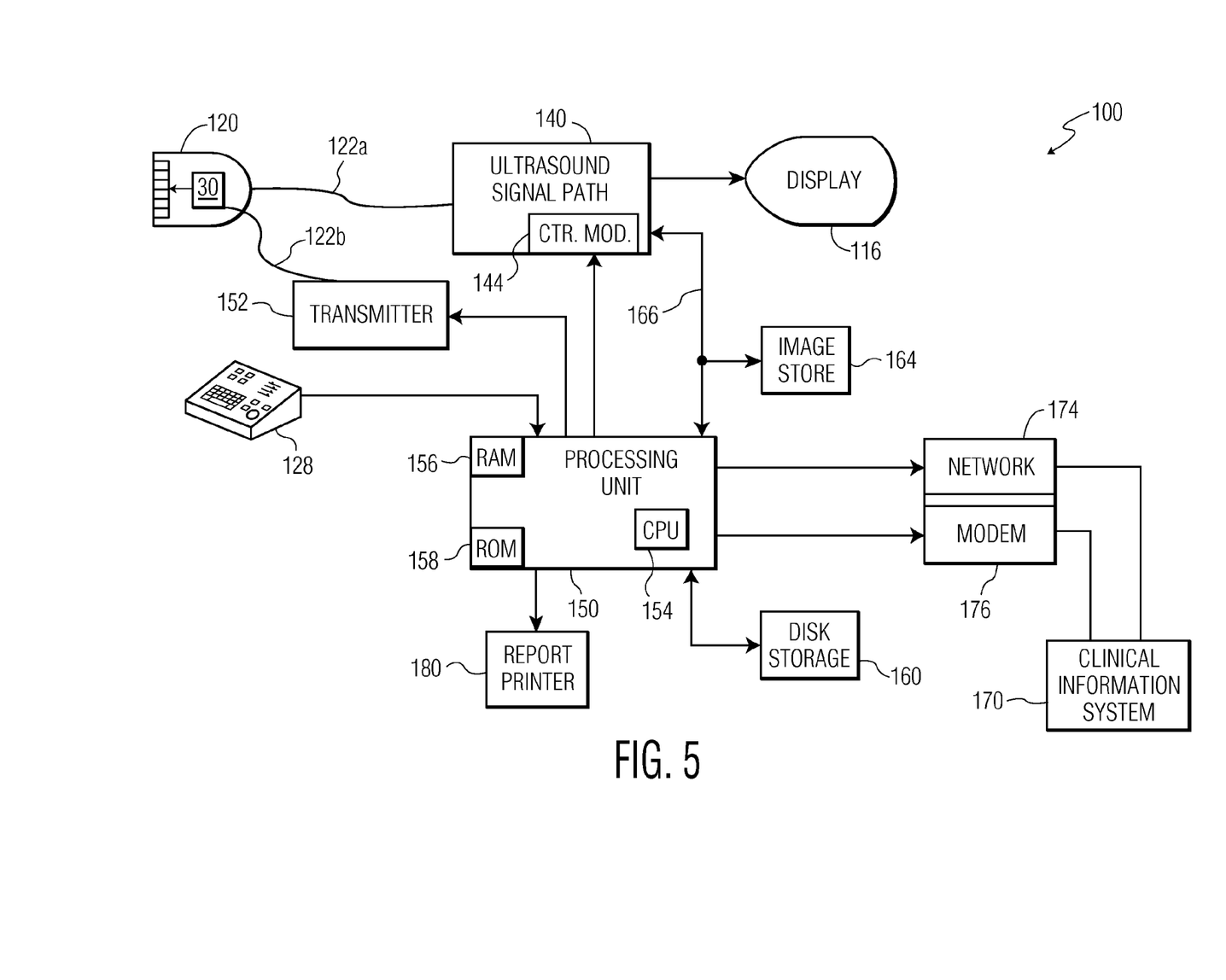
FIG. 5 is a block diagram of the electrical components used in the ultrasound system of FIG. 4.

The electrical components of the ultrasound system 100 are illustrated in FIG. 5. The imaging elements 14 of the ultrasound transducer 120 are coupled by the cable 122*a* to an ultrasound signal path 140 of conventional design. As is well-known in the art, the ultrasound signal path 140 includes a transmitter (not shown) coupling electrical signals to the imaging elements 14, an acquisition unit (not shown) that receives electrical signals from the imaging elements 14 corresponding to ultrasound echoes, a signal processing unit (not shown) that processes the signals from the acquisition unit to perform a variety of functions, such as isolating returns from specific depths or isolating returns from blood flowing through vessels, and a scan converter (not shown) that converts the signals from the signal processing unit so that they are suitable for use by the display 116. The processing unit in this example is capable of processing both B mode (structural) and Doppler signals for the production of B mode and Doppler images. The ultrasound signal path 140 also includes a control module 144 that interfaces with a processing unit 150 to control the operation of the above-described units. The ultrasound signal path 140 may, of course, contain components in addition to those described above, and, in suitable instances, some of the components described above may be omitted.

The ultrasound system 100 also includes a transmitter 152 that is coupled by the cable 122*b* to the RF amplifier 30, which is, in turn, coupled to the therapy transducer elements in the transducer 120. The transmitter 152 is connected to the processing unit 150, which supplies signals to the transmitter 152 to initiate the transmission of signals from the transmitter 152. If desired, the signals from the processing unit 150 may also control the delay of the signals applied to the therapy elements in the transducer probe 120 either to scan in elevation or azimuth or to focus the therapeutic ultrasound to a specific depth.

The processing unit 150 contains a number of components, including a central processor unit ("CPU") 154, random access memory ("RAM") 156, and read only memory ("ROM") 158, to name a few. As is well-known in the art, the ROM 158 stores a program of instructions that are executed by the CPU 154, as well as initialization data for use by the CPU 154. The RAM 156 provides temporary storage of data and instructions for use by the CPU 154. The processing unit 150 interfaces with a mass storage device such as a disk drive 160 for permanent storage of data, such as data corresponding to ultrasound images obtained by the system 100. However, such image data is initially stored in an image storage device 164 that is coupled to a signal path 166 extending between the ultrasound signal path 140 and the processing unit 150. The disk drive 160 also preferably stores protocols which may be called up and initiated to guide the sonographer through various ultrasound examination and/or therapy protocols.

The processing unit 150 also interfaces with the keyboard and controls 128. The keyboard and controls 128 may also be manipulated by a sonographer or other individual to cause the ultrasound system 100 to produce automatically generated reports at the conclusion of an examination and/or therapy. The processing unit 150 preferably interfaces with a report printer 180 that prints reports containing text and one or more images and/or therapy reports. Finally, data corresponding to an image or therapy may be downloaded through a suitable data link, such as a network 174 or a modem 176, to a clinical information system 170 or other device.

An imaging and therapy transducer probe 10,50 which includes amplifiers integrated into the probe, preferably located in the probe connector 32 as described above, can be operated by a standard imaging ultrasound system by partitioning the channels of the beamformer of the ultrasound signal path 140 between the imaging and therapy functions. For example, if the therapy transducer has eight transducer elements, those elements can be controlled by eight channels of the beamformer with the other beamformer channels dedicated to imaging. A conventional 128 channel beamformer could be programmed to use eight of its channels for controlling the therapy elements and the other 120 channels for operating the imaging transducer array. For an imaging and therapy probe with a greater number of therapy elements, such as one with elevational steering capabilities, 32 channels of the beamformer could be devoted to therapy and 96 channels devoted to imaging. Other ratios may be chosen depending upon the specific makeup of the transducer arrays and the beamformer.

Figure 6:
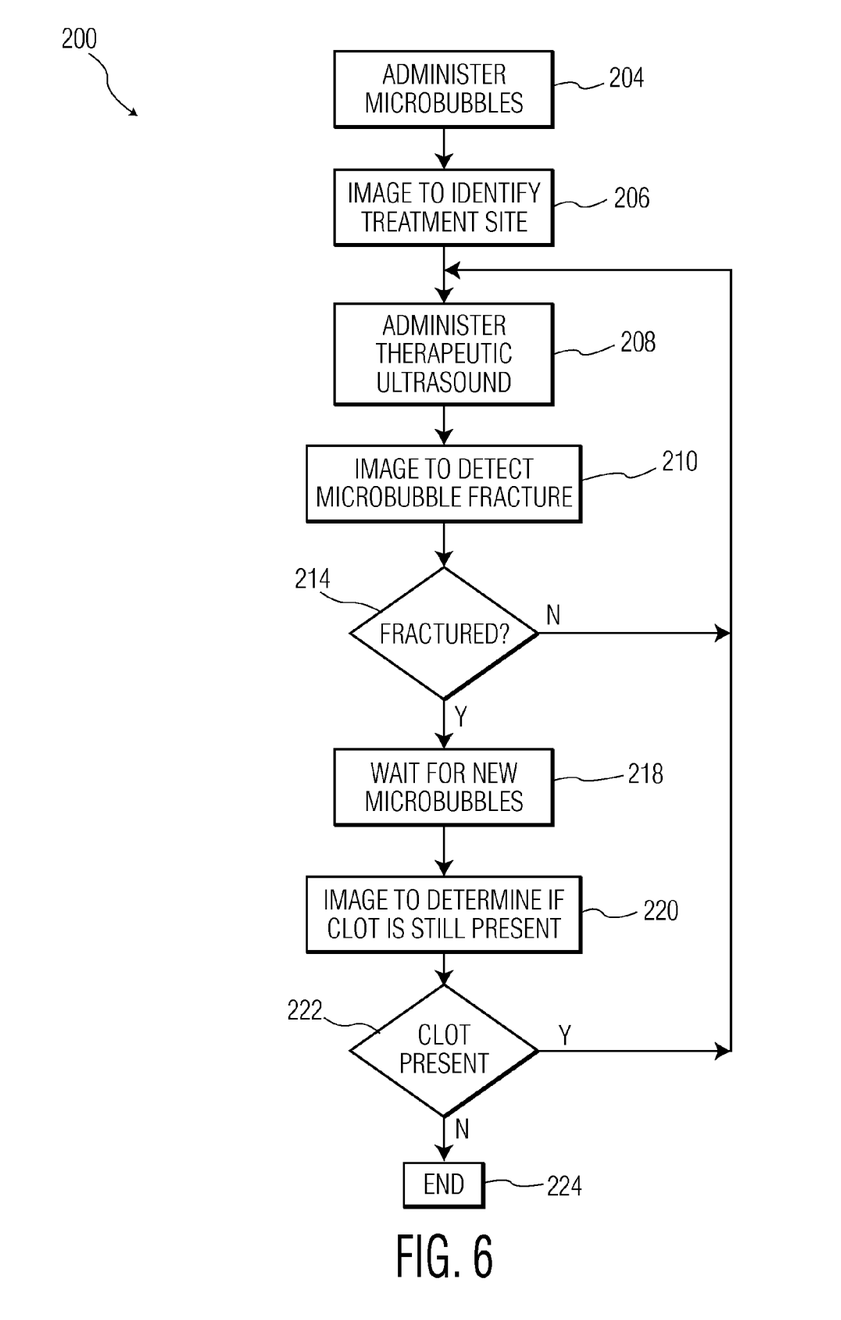
FIG. 6 is a flow chart showing a method of using the ultrasound system of FIGS. 4 and 5 or some other ultrasound system to dissolve blood clots according to one example of the invention.

One example of a technique 200 for using the ultrasound system 100 with the ultrasound transducer probe 120 (FIGS. 4 and 5) to dissolve a clot is illustrated in FIG. 6. As explained above, the transducer probe 120 may include one of the transducers 10, 50 or a transducer according to some other example of the invention. A microbubble contrast agent is initially administered at step 204. After sufficient time has lapsed for the contrast agent to reach an area of interest where a clot may be present, the transducer probe 120 is used to image the region of interest at step 206. The presence of a clot can be detected by the lack of blood flowing through a vein in the region of interest. Once a clot has been located, therapy is initiated at step 208 by triggering the transmitter 152 (FIG. 5) to apply signals to the RF amplifier 30 in the transducer probe 120. The RF amplifier 30 then applies high-intensity signals to the ultrasound therapy elements in the transducer probe 120.

After a short period of therapy has been administered at step 208, the transducer probe 120 is again used to image the treatment site at step 210. A check is then made at step 214 to determine if all of the microbubbles at the site have been fractured. If not, the process returns to step 208 and continues to loop through steps 208, 210 and 214 until all of the microbubbles have been fractured.

The interleaving of imaging ultrasound with therapeutic ultrasound at steps 208, 210 and 214 preferably occurs with a relatively small therapeutic ultrasound duty cycle. In one example of the ultrasound system 100, the step 208 of administering the therapeutic ultrasound has a duration of 0.5 seconds followed by the step 210 of imaging having a duration of 10 seconds. The therapeutic ultrasound in this example thus has a duty cycle of $\frac{1}{20}$. During the ten second imaging period the clinician will observe the blood vessel where the microbubbles were disrupted to see if microbubbles remain at the site for another period of disruption. The ten second interval allows approximately ten heart cycles to replenish the therapy location with a flow of new microbubbles. The clinician may adjust the therapy interval to be longer or shorter. Generally, the clinician will want to apply therapy ultrasound for as long as microbubbles remain at the site of the clot. Continuous wave (CW) ultrasound has been found to grow microbubbles in size by the phenomenon known as rectified diffusion by which the microbubbles will draw in dissolved gas from the surrounding tissue and blood. Hence, a clinician may want to apply ultrasound at the appropriate level for a period of time to allow microbubbles to increase in size by this phenomenon. The clinician may also want to have a longer imaging period so the microbubbles at the clot can be observed for awhile. Consequently a completely manual operation may be preferred, where a control on the ultrasound system is actuated for as long as the clinician wants to apply therapy energy. When the clinician is not actuating the control the ultrasound system controls the probe to image the therapy location. In this way the clinician can apply therapy whenever he wants and for as long as he wants. Since the degree and speed of microbubble disruption and replenishment will vary from vessel to vessel and from patient to patient, a manually controlled procedure is often preferred.

Fracturing of the microbubbles can be detected using a variety of techniques. For example, the image created at step 210 can be examined to determine the intensity of the echoes reflected from the treatment site. The echoes will initially be very intense. But as fracturing of the microbubbles continues, the intensity of the echoes will diminish. At some threshold level, substantially all of the microbubbles can be considered to be fractured. Another technique is to examine the oscillation pattern of the microbubbles. When the therapeutic ultrasound insonifies the microbubbles at step 208, the microbubbles will oscillate at a characteristic frequency. This oscillation can be detected using the imaging elements 14 during the imaging step 210 to provide an indication that the microbubbles are still present. Other techniques can also be used.

Regardless of how rapidly disruption or fracture of the microbubbles occurs, at some point substantially compete fracture will be detected at step 214, and the process will advance to step 218 to wait for new microbubbles to perfuse the treatment site. The treatment site is imaged at 220 to determine if microbubbles have again perfused the treatment site. As the clot at the treatment site starts to dissolve, the microbubbles will perfuse the site more quickly. The need to continue the therapy to dissolve the clot thus is detected at step 222 by the failure of the microbubbles to perfuse the clot after a predetermined period, or by the resumption of blood flow through a previously occluded vessel. If the determination is made at step 222 that the clot is still present, the process returns to step 208 for additional therapy. The above-describe process is continuously repeated until the clot is no longer detected at step 222. The process then ends at step 224.

Another imaging and therapy technique is to disrupt or burst the microbubbles for a limited period and then, while microbubbles remain at the treatment site, imaging the site for a short period while microbubbles are replenished by the blood flow. For instance, if it takes 20 seconds to disrupt or burst 95% of the microbubbles at the treatment site, it may be the case that two-thirds of the microbubbles are burst or disrupted in ten seconds. Thus, a procedure may commence with 10 seconds of therapy pulses which burst or disrupt two-thirds of the microbubbles present at the site, followed by a seven second imaging interval (about seven heart cycles) during which approximately the original microbubble density is restored. Therapy and imaging would then alternate in this ten second/seven second sequence.

The characteristics of the transducers 10, 50 particularly lend themselves to the imaging and therapy process 200 shown in FIG. 6. By precisely overlapping the imaging and therapy regions, the transducer 120 ensures that the region imaged is the region receiving the therapy. Insofar as there is no need to move the transducer probe 120, the ultrasound system 100 can quickly switch between imaging and therapy. Another variation which can be practiced with the multi-element therapy transducer is to steer or sweep the focal region of the therapy ultrasound from side to side in the blood vessel in the elevation direction to more efficiently burst or disrupt the microbubbles over the entire clot. Other advantages inherent in the characteristics of the transducer probe 120 will be apparent to one skilled in the art.

Although the present invention has been described with reference to the disclosed embodiments, persons skilled in the art will recognize that changes may be made in form and detail without departing from the spirit and scope of the invention. Such modifications are well within the skill of those ordinarily skilled in the art. Accordingly, the invention is not limited except as by the appended claims.

We claim:

1. An ultrasound transducer probe operable with an ultrasound system for imaging and therapy, comprising:
a linear array of imaging transducer elements extending longitudinally in an azimuthal direction and operable to image an image plane;

a first linear therapy array of therapy transducer elements extending longitudinally in an azimuthal direction along a first side of the linear array of imaging transducer elements;

a cable having a distal end coupled to the arrays linear array of imaging transducer elements and the first linear therapy array of therapy transducer elements; and a connector coupled to the proximal end of the cable which is operable to connect the probe to beamformer channels of the ultrasound system, the connector including a high intensity amplifier electrically coupled by the cable to the linear array of therapy elements which supplies high intensity electrical signals to the therapy elements.

2. The ultrasound transducer probe of claim 1, wherein the amplifier comprises a plurality of amplifiers electrically coupled to a plurality of the therapy transducer elements of the therapy array.

3. The ultrasound transducer probe of claim 2, further comprising:

a second linear therapy array of therapy transducer elements extending longitudinally in an azimuthal direction along a second side of the linear array of imaging transducer elements opposite the first side, the first and second linear therapy arrays of therapy transducer elements transmitting ultrasound waves which are transmitted inwardly toward the image plane, wherein a plurality of amplifiers are coupled to a plurality of therapy transducer elements of the therapy arrays.

4. The ultrasound transducer probe of claim 3, wherein the number of therapy transducer elements extending along the first and second sides of the linear array of imaging transducer elements is substantially less than the number of imaging transducer elements.

5. The ultrasound transducer assembly of claim 4 wherein the imaging transducer elements are structured to operate at a substantially higher frequency than a frequency at which the therapy transducer elements are structured to operate.

6. An ultrasound imaging and therapy system, comprising:
an ultrasound transducer probe, comprising:
a linear array of imaging transducer elements extending longitudinally in an azimuthal direction;
a first linear array of therapy transducer elements extending longitudinally in an azimuthal direction along a first side of the linear array of imaging transducer elements; and
an ultrasound system, comprising:
an ultrasound signal path including a beamformer having a total number of beamformer channels, with a first plurality of the total number of beamformer channels coupled to operate the linear array of imaging transducer elements during imaging and a second plurality of beamformer channels coupled to operate the linear array of therapy transducer elements during therapy, the ultrasound signal path transmitting electrical signals to the imaging transducer elements to cause the imaging transducer elements to transmit ultrasound into a region of interest beneath the first linear array of imaging transducer elements, the ultrasound signal path further receiving electrical signals indicative of ultrasound reflections from the region of interest and to process the received electrical signals;
a display coupled to the ultrasound signal path to provide an image corresponding to the electrical signals received from the imaging transducer elements and processed by the ultrasound signal path; and
a cable coupled at a distal end to the linear array of imaging transducer elements and the first linear therapy array of therapy transducer elements and at a proximal end to a probe connector which acts to couple the ultrasound transducer probe to the beamformer of the ultrasound system, wherein a high-intensity amplifier is housed in the connector and coupled to the therapy transducer elements.

7. The ultrasound imaging and therapy system of claim 6 wherein the ultrasound signal path is operable to scan the region of interest by successively applying the electrical signals to and receiving the electrical signals from the imaging transducer elements from one end of the first array to the other.

8. The ultrasound imaging and therapy system of claim 6 wherein the ultrasound signal path is operable to delay the signals received from the imaging transducer elements to steer the ultrasound received by the first array of imaging transducer elements in the azimuthal direction.

9. The ultrasound imaging and therapy system of claim 6 wherein the ultrasound signal path is operable to delay the signals received from the imaging transducer elements to focus the ultrasound received by the first array of imaging transducer elements to a specific depth in the region of interest.

10. The ultrasound imaging and therapy system of claim 6, further comprising a second linear array of therapy transducer elements extending longitudinally in an azimuthal direction along a second side of the linear array of imaging transducer elements opposite the first side, the first and second linear arrays of therapy transducer elements transmitting ultrasound waves which are transmitted inwardly toward an image plane of the imaging transducer elements.

11. The ultrasound imaging and therapy system of claim 10 wherein the number of therapy transducer elements extending along the first and second sides of the linear array of imaging transducer elements is substantially less than the number of imaging transducer elements.

12. An ultrasound imaging and therapy system, comprising:
an ultrasound transducer probe, comprising:
a linear array of imaging transducer elements extending longitudinally in an azimuthal direction;
a first linear array of therapy transducer elements extending longitudinally in an azimuthal direction along a first side of the linear array of imaging transducer elements; and
an ultrasound system, comprising:
an ultrasound signal path having beamformer channels partitioned between and coupled to operate the linear array of imaging transducer elements during imaging and the linear array of therapy transducer elements during therapy for disrupting/destroying microbubbles in the vicinity of a blood clot;
a display coupled to the ultrasound system and operable to display images produced in response to signals received from the imaging transducer elements;
a user control, coupled to the array of therapy transducer elements and operable by a user to cause the array of therapy transducer elements to transmit therapeutic ultrasound waves when actuated by a user; and
an amplifier responsive to the user control and coupled to the therapy transducer elements to cause the therapy transducer elements to transmit the therapeutic ultrasound waves when actuated by the user control, wherein the ultrasound transducer probe further comprises a connector which is operable to connect the probe to the beamformer channels of the ultrasound system, and wherein the amplifier is located in the connector.

13. The ultrasound imaging and therapy system of claim 12 wherein the amplifier further comprises a plurality of amplifiers electrically coupled to the therapy transducer elements.

\* \* \* \* \*